(12) United States Patent
Mantz et al.

(10) Patent No.: US 8,450,215 B2
(45) Date of Patent: May 28, 2013

(54) PARTICLE BEAM SYSTEMS AND METHODS

(75) Inventors: Hubert Mantz, Neu-Ulm (DE); Rainer Arnold, Ulm (DE); Michael Albiez, Aalen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 315 days.

(21) Appl. No.: 12/806,111

(22) Filed: Aug. 5, 2010

(65) Prior Publication Data

US 2011/0031215 A1     Feb. 10, 2011

(30) Foreign Application Priority Data

Aug. 7, 2009 (DE) .................. 10 2009 036 701

(51) Int. Cl.
    *H01L 21/302*        (2006.01)
    *H01L 21/461*        (2006.01)

(52) U.S. Cl.
    USPC ........... 438/706; 438/707; 438/710; 438/712; 438/714

(58) Field of Classification Search
    None
    See application file for complete search history.

(56) References Cited

U.S. PATENT DOCUMENTS

| | | | |
|---|---|---|---|
| 3,030,512 A | 4/1962 | Harker | |
| 3,100,261 A | 8/1963 | Bigelow | |
| 3,204,095 A | 8/1965 | Watanabe | |
| 5,525,806 A | 6/1996 | Iwasaki et al. | |
| 5,847,388 A | 12/1998 | Foote et al. | |
| 5,903,004 A | 5/1999 | Koshihara et al. | |
| 5,943,388 A | 8/1999 | Tuemer | |
| 6,855,938 B2 | 2/2005 | Preikszas et al. | |
| 2002/0024014 A1 | 2/2002 | Kazumori | |
| 2003/0089852 A1 | 5/2003 | Ochiai et al. | |
| 2003/0189172 A1 | 10/2003 | Sawahata et al. | |
| 2004/0043621 A1* | 3/2004 | Nasser-Ghodsi | 438/710 |
| 2004/0245464 A1* | 12/2004 | Iwasaki et al. | 250/307 |
| 2005/0184251 A1 | 8/2005 | Oi et al. | |
| 2006/0138325 A1 | 6/2006 | Choi | |
| 2007/0104320 A1 | 5/2007 | Arenson et al. | |
| 2007/0215802 A1 | 9/2007 | Ward et al. | |
| 2007/0228287 A1 | 10/2007 | Ward et al. | |
| 2008/0042057 A1* | 2/2008 | Sanada et al. | 250/305 |

FOREIGN PATENT DOCUMENTS

| | | |
|---|---|---|
| DE | 697 09 307 T2 | 6/2002 |
| DE | 10 2005 061 663 A1 | 7/2007 |
| DE | 10 2009 024 928 A1 | 10/2010 |
| DE | 102009024928 A1 | 10/2010 |
| EP | 0 865 662 B1 | 12/2001 |
| EP | 1227315 A2 | 12/2001 |

(Continued)

OTHER PUBLICATIONS

Extended European search report dated Dec. 7, 2011 from European patent application No. 10 008 253.6.

(Continued)

*Primary Examiner* — Duy Deo
(74) *Attorney, Agent, or Firm* — Bruce D. Riter

(57) ABSTRACT

An inspection method comprises
focusing a particle beam onto a sample;
operating at least one detector located close to the sample;
assigning detection signals generated by the at least one detector to different intensity intervals;
determining, based on the detection signals assigned to the intensity intervals, at least one first signal component related to electrons incident on the detector; and
determining, based on the detection signals assigned to the intensity intervals, at least one second signal component related to X-rays incident on the detector.

20 Claims, 6 Drawing Sheets

FOREIGN PATENT DOCUMENTS

| | | |
|---|---|---|
| EP | 2105944 A1 | 3/2008 |
| GB | 899 291 A | 6/1962 |
| GB | 2295454 A | 5/1996 |
| JP | 56153656 A | 11/1981 |
| JP | 57069655 A | 4/1982 |
| JP | 03216581 A | 9/1991 |
| JP | 06283132 A | 10/1994 |
| JP | 2003 217 497 A | 7/2003 |
| WO | 8103707 | 12/1981 |
| WO | WO 2008/051880 A2 | 5/2008 |
| WO | WO 2008/051937 A2 | 5/2008 |
| WO | 2010115873 A1 | 10/2010 |

OTHER PUBLICATIONS

P.R. Munroe et al., "The application of focused ion beam microscopy in the material sciences", Materials Characterization, Elsevier, New York, US, vol. 60, No. 1, Jan. 1, 2009, pp. 2-13.

Extended European Search Report dated May 11, 2012 in European Patent Application No. 10 001 335.8.

Wlodzimierz Drzazga at al., "Three-dimensional characterization of microstructures in a SEM", Measurement Science and Technology 17 (2006), pp. 28-31.

L. Reimer, "Scanning Electron Microscopy", Optical Sciences, Physics of Image Formation and Microanalysis, Second Edition, Springer (1998), Kapitel 10.1 & 10.2, pp. 379-407.

Lowe B G Ed—Eds : David B Williams et al: Chapter 2: Problems and Trends in X-Ray Detector Design for Microanalysis: Jan. 1, 1995, X-Ray Spectrometry in Electron Beam Instruments, Plenum Press, pp. 7-19 , XP009136042 ISBN: 978-0-306-44858-4.

Partial European search report dated Sep. 15, 2011 from European patent application No. 10 008 253.6.

A.R. Wilson et al., "Backscattered electron effects in a high-angle EDXS", Journal of Physics E. Scientific Instruments, IOP Publishing, Bristol, GB, vol. 22, No. 9, Sep. 1, 1989, pp. 726-729.

R. Cossio et al., "Improvements in trace element detection in energy dispersive spectrometry using an X-ray filter (FEDS) and applications to petrological problems", Microchimica Acta, An International Journal on Micro And Traceanalysis, Springer-Verlag, VI, vol. 161, No. 3-4, Dec. 20, 2007, pp. 337-342.

R.T. Murray, "A filter to remove backscattered electrons for energy-dispersive analysis in a scanning microscope", Journal of Physics E. Scientific Instruments, IOP Publishing, Bristol, GB, vol. 12, No. 12, Dec. 1, 1979, p. 1141.

M. Schaffer et al., "Automated three-dimensional X-ray analysis using a dual-beam FIB", Ultramicroscopy, Elsevier, Amsterdam, NL, vol. 107, No. 8, Apr. 21, 2007, pp. 587-597.

W. Drzazga et al., "Three-dimensional characterization of microstructures in a SEM", Measurement Science and Technology, IOP, Bristol, GB, vol. 17, No. 1, Jan. 1, 2006, pp. 28-31.

Office Action dated Sep. 14, 2012 in European patent application No. 10 008 253.6, 4 pages.

\* cited by examiner

PARTICLE BEAM SYSTEMS AND METHODS

CROSS-REFERENCES TO RELATED APPLICATIONS

The present application claims priority of Patent Application No. 10 2009 036 701.2, filed Aug. 7, 2009 in Germany, entitled "Teilchenstrahlsystem and Untersuchungsverfahren hierzu", the contents of which is hereby incorporated by reference in its entirety.

This application is related to U.S. patent application Ser. No. 12/658,476 filed Feb. 8, 2010 and to U.S. patent application Ser. No. 13/247,979 filed Sep. 28, 2011 and to U.S. patent application Ser. No. 13/247,995 filed Sep. 28, 2011.

FIELD

The present disclosure relates to particle beam systems using a particle beam, wherein the particle beam can be, for example, an electron beam and an ion beam. The present disclosure further relates to inspection methods for obtaining information relating to a structure of a sample using a particle beam.

BACKGROUND

A conventional particle beam microscope comprises a particle beam source for generating a primary particle beam, and an electron detector. Examples of such particle beam microscopes include an electron microscope having an electron beam source and an ion microscope having an ion beam source. An electron microscope may have a X-ray detector for detecting X-rays generated by the primary particle beam incident on the sample. The X-rays may include characteristic X-rays indicative of chemical elements contained in the sample such that an elemental composition of the sample can be determined from an analysis of detection signals generated by the X-ray detector, wherein the analysis may include an analysis of an energy of detected X-rays. Such method is known as energy dispersive X-ray spectroscopy (EDX).

It is desirable to improve inspection methods and inspection systems using a combination of an electron detection and an X-ray detection.

SUMMARY

It is an object of the present disclosure to provide an inspection method and an inspection system in which information relating to a sample can be obtained from both electrons and X-rays emanating from the sample.

According to embodiments, a detector is used which can detect both electrons and X-rays and which is arranged close to the sample. This detector generates detection signals corresponding to incident electrons and X-rays. By analyzing a larger number of detection signals it is possible to separate a signal component related to electrons incident on the detector from a signal component related to X-rays incident on the detector.

According to embodiments, an analysis of detection signals comprises an analysis of an intensity spectrum or an energy spectrum of the detection signals.

According to embodiments, an analysis of detection signals comprises assigning detection signals generated by the detector to plural different intensity intervals, determining, based on the detection signals assigned to the intensity intervals, at least one first signal component related to electrons incident on the detector, and determining, based on the detection signals assigned to the intensity intervals, at least one second signal component related to X-rays incident on the detector.

Herein, the detector may be configured such that detection signals generated by the detector vary with respect to their intensities, wherein the intensities depend on an intensity of a detected event. If the detected event is an electron incident on the detector, its intensity will depend on the kinetic energy of the electron which is incident on the detector. The intensity of the detection signal will represent the kinetic energy of the detected electron, accordingly. Similarly, if the detected event is a X-ray incident on the detector, the intensity of the detection signal will represent the energy of the incident X-ray.

Different detection signals may differ with respect to their intensity since they cause, depending on a type of the detector, different electric voltages, different electric currents, different electric resistances, different electric charge amounts or other different effects at an output of the detector. The different electric voltages, currents, resistances, charge amounts and other effects can be amplified, transformed and further processed by electric circuits connected to the output of the detector.

According to embodiments, the detection signals of the detector are assigned to intensity intervals. The intensity intervals may correspond to energy intervals of the detected events. The intensity intervals may partially overlap, or the intensity intervals can be disjoint.

According to embodiments, a counter is assigned to each intensity interval to count a number of detection signals having an intensity falling within the respective intensity interval.

According to embodiments herein, a multi-channel analyzer can be used to assign the detection signals to intensity intervals.

An energy spectrum of the detected events can be determined by counting the detection signals assigned to respective intensity intervals and displaying the counts according to increasing intensities of the intensity intervals, for example.

The energy spectrum represents two types of events, i.e. the incidence of electrons on the detector and the incidence of X-rays on the detector. The incident electrons result in a broad spectral peak having a maximum and a width of several keV. The incident X-rays result in one or more spectral peaks having a maximum and a width of less than 1 keV. It is apparent that signal components related to electrons incident on the detector can be separated from signal components related to X-rays incident on the detector based on an analysis of the energy spectrum due to the different spectral properties of the electron events and the X-ray events. Even though the concept of the energy spectrum is very illustrative for understanding the separation of signal components related to electrons from signal components related to X-rays, it is not necessary to explicitly determine the energy spectra in practice. It is possible to perform a corresponding analysis directly, without determining the energy spectrum and based on assigning detection signals to different intensity intervals.

According to embodiments, at least one chemical element contained in the sample is determined based on at least one signal component related to X-rays incident on the detector and determined based on detection signals assigned to intensity intervals. In a representation as an energy spectrum, narrow maxima of the signal components related to X-rays are indicative of a presence of chemical elements in the sample at a location onto which the particle beam is focused. It is possible to determine chemical elements present at that location of the sample by analyzing the maxima of the energy spectrum. Again it is possible to determine the chemical elements present at the location of the sample by assigning the detection signals to the different intensity intervals, without calculating an energy spectrum.

According to embodiments, the focused particle beam is subsequently directed to plural different locations of the sample. According to particular embodiments herein, the focused particle beam is scanned across the sample.

According to further embodiments herein, a method as illustrated above is performed for each of the different locations, such that, for each location at which the particle beam is focused, a plurality of detection signals is assigned to intensity intervals in order to separate signal components related to electrons from signal components related to X-rays. The signal components related to electrons represent an electron microscopic image of the sample, whereas the signal components related to X-rays represent an image or a map of an elemental composition of the sample. These images can be displayed either individually or in superposition with each other.

According to embodiments, plural detectors are arranged close to the sample. The plural detectors may differ with respect to their positions relative to the sample. For example, the different detectors may cover different solid angles relative to the sample. The information obtained from detection signals of the different detectors may then be used to determine a three-dimensional structure of the sample.

The plural detectors may also differ with respect to their detection sensitivity for detecting electrons and X-rays. According to embodiments, membranes are arranged between the detectors and the sample, wherein the membranes differ with respect to their transmission characteristics for electrons and X-rays. According to embodiments herein, the membranes differ with respect to their thickness or their chemical composition.

BRIEF DESCRIPTION OF THE DRAWINGS

The forgoing as well as other advantageous features of this disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
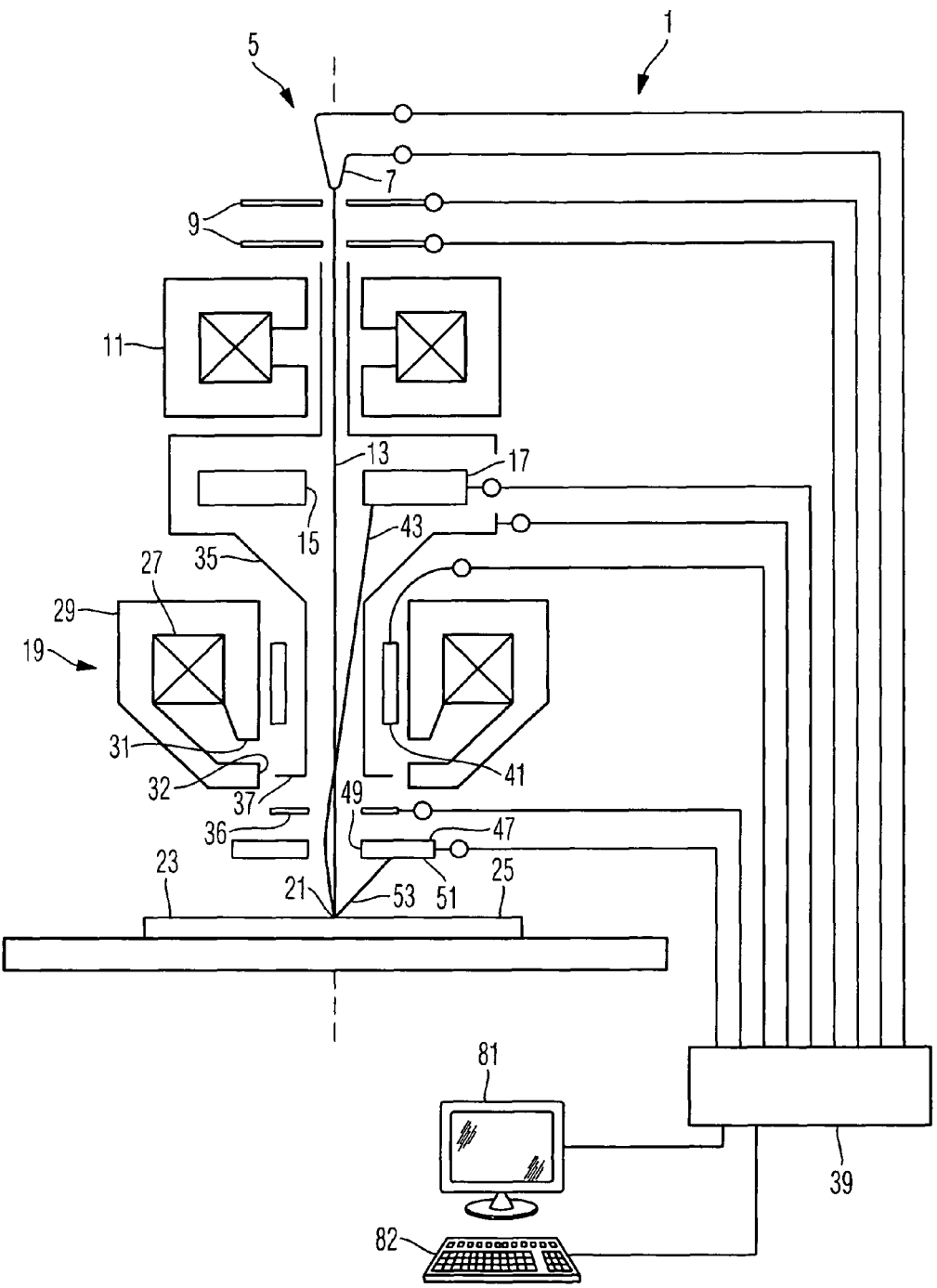
FIG. 1 shows a particle beam system according to an embodiment.

In the exemplary embodiments described below, components that are alike in function and structure are designated as far as possible by alike reference numerals. Therefore, to understand the features of the individual components of a specific embodiment, the descriptions of other embodiments and of the summary should be referred to.

FIG. 1 is a schematic illustration of an exemplary embodiment of a particle beam system 1. The particle beam system 1 comprises an electron beam source 5 having a cathode 7 and extractor and suppressor electrodes 9 for generating a primary particle beam 13. The primary particle beam 13 traverses a condenser lens 11, an aperture 15 provided in an electron detector 17, and an objective lens 19 for focusing the primary particle beam 13 at a location 21 in an object plane 23. A surface of an object 25 to be inspected is disposed in the object plane 25.

The objective lens 19 comprises a ring coil 27 provided in a ring-shaped yoke having a ring-shaped upper pole piece 31 and a ring-shaped lower pole piece 32 such that a ring-shaped gap is formed between the upper and lower pole pieces 31, 32. A magnetic field for generating the electron beam 13 is generated in this gap.

The particle beam system 1 further includes a beam tube 35 which enters and partially traverses the objective lens 19. An end electrode 37 is provided at a bottom end of the beam tube 35. A terminal electrode 36 is disposed between the end electrode 37 and the object plane, wherein an electrostatic field generated between the end electrode 37 and terminal electrode 36 provides a focusing power on the primary electron beam 13. The focusing power provided by the electrostatic field between the electrodes 36 and 37 and the focusing power provided by the magnetic field between the pole pieces 31 and 32 commonly provide the focusing power of the objective lens 19 of the particle beam system 1.

A controller 39 is provided for supplying suitable voltages to the terminal electrode 36, the end electrode 37, the cathode 7 and the extractor and suppressor electrodes 9 such that an electron beam focus is formed in the object plane.

These voltages can be selected such that the electrons of the primary electron beam have a predetermined kinetic energy when they are incident on the object 25 at location 21. It is in particular possible that the controller 39 supplies a voltage corresponding to ground potential or a voltage differing from ground potential to the terminal electrode 36.

The objective lens 19 further includes deflectors 41 which are also controlled by the controller 39 for deflecting the electron beam 13 and for varying the location 21 at which the primary electron beam 13 is incident on the object 25 in the object plane 23. By deflecting the primary electron beam it is in particular possible to systematically scan the primary particle beam across a portion of the surface of the object 25.

The primary particle beam incident on the object 25 results in that secondary electrons emerge from the object 25. A portion of such secondary electrons may enter into the beam tube 35 such that they are detected by the electron detector 17. In the context of the present disclosure, the term secondary electrons comprises all types of electrons which are caused to emerge from the object by directing the primary particle beam onto the object and which can be detected by the electron detector 17. The term secondary electrons in particular comprises backscattered electrons having a kinetic energy which corresponds to or is somewhat smaller than the kinetic energy of the primary particles incident on the object. The term further comprises secondary electrons having, when they emerge from the surface of the object, a kinetic energy which is substantially smaller than the kinetic energy of the primary particles upon their incidence onto the object. FIG. 1 schematically shows an exemplary trajectory of a secondary electron which is incident on the electron detector 17 at reference numeral 43.

The particle beam system 1 further comprises a further detector 47 disposed in between of the objective lens 19 and the object plane 23. The detector 47 comprises a central aperture 49 allowing the primary particle beam 13 and secondary electrons 43 to traverse the detector 47. The detector 47 comprises plural detection surfaces 51 located at a radial distance from a main axis 12 of the objective lens. The detector 47 is provided for detecting both secondary electrons and X-rays generated by the primary particle beam 13 incident on the object. An exemplary trajectory of a secondary electron or X-ray generated by the primary electron beam 13 at location 21 and incident on the detector 47 is indicated in FIG. 1 at reference numeral 53.

Figure 2:
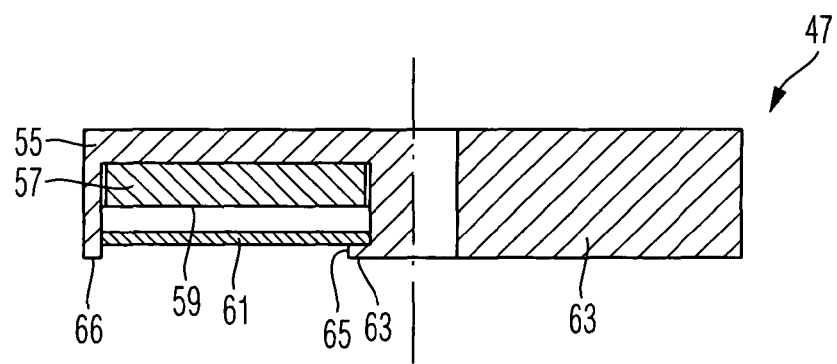
FIG. 2 shows a cross section of a detector of the particle system shown in FIG. 1 along a line II-II in FIG. 3.
Figure 3:
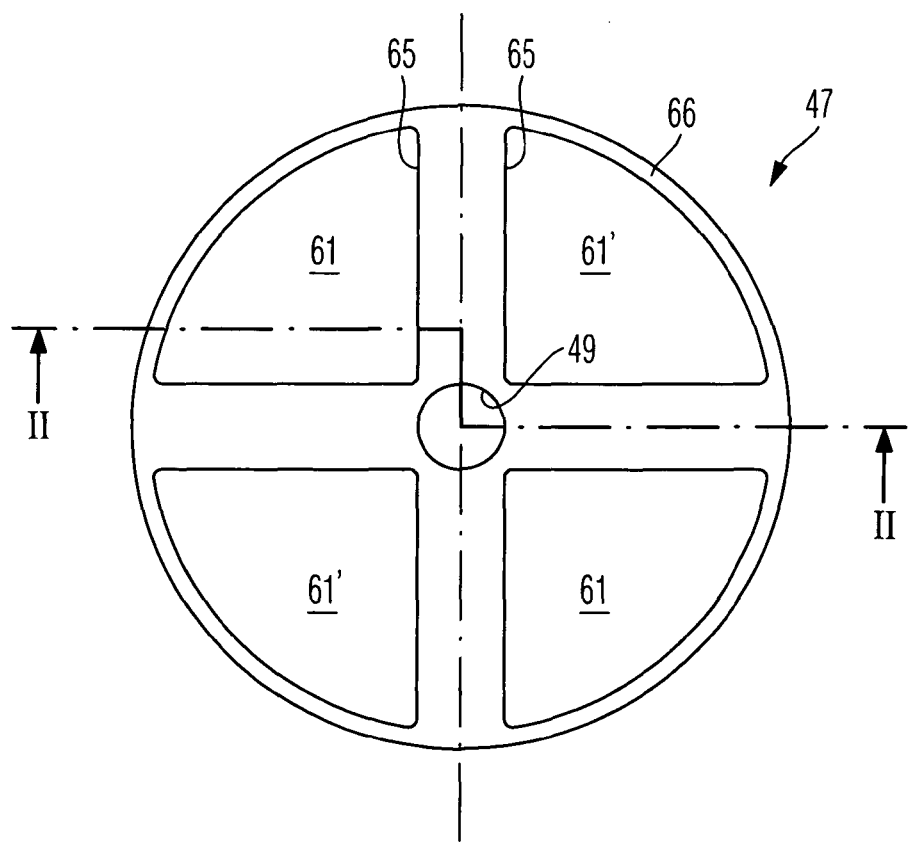
FIG. 3 is an elevational view from the bottom of the detector shown in FIG. 2.

A configuration of the detector 47 is illustrated as a sectional view in FIG. 2 and as an elevational view in FIG. 3. The detector 47 comprises a ring-shaped carrier including an upper plate 55 having a central bore for providing the aperture 49 allowing the primary particle beam 13 and the secondary electrons 43 to pass through. Four semiconductor detectors are attached to a bottom surface of plate 55 such that a detection surface 59 of each semiconductor detector 57 is oriented towards the object plane 23. A membrane or window 61 is mounted in front of the detection surface 59 of each semiconductor detector 57. The membranes 61 have a function to at least partially prevent incidence of secondary electrons on the detection surfaces 59 of the semiconductor detectors 57. In the exemplary embodiment shown in FIG. 2, the membrane 61 is disposed at a small distance from the detection surface 59. It is, however, also possible that the membrane contacts or is directly attached as a membrane layer to the detection surface of the semiconductor detector and such that the membrane is carried by the semiconductor detector.

The semiconductor detector can be a silicon drift detector, such as a detector obtainable under the product name Xflash® QUAD from Bruker AXS Microanalysis GmbH, Berlin, Germany.

The membranes 61 can be configured such that they are not fixedly attached to the semiconductor detector or the ring structure such that they can be readily removed and replaced by other membranes. The exemplary embodiment shown in FIGS. 2 and 3 has axial projections 63 provided on the plate 55. The projections 63 include radially extending portions 65 adapted to carry the membranes 61 such that they are mounted on the detector 47. For example, the membranes 61 can be clamped between the radial projections 65 and an outer axial ring-shaped projection 66 provided on the plate 55.

In the embodiment shown in FIGS. 2 and 3, the X-ray detector 57 comprises four separate semiconductor detectors 57 arranged in a configuration of four quadrants distributed around the aperture 49. The four semiconductor detectors 57 each have a same configuration and same properties, and detection signals of the four semiconductor detectors 57 are separately received by the controller 39.

In the example shown in FIGS. 2 and 3, the detection surface of the detector is ring-shaped, traversed by the primary beam and located close to the location 21 of incidence of the particle beam 13 on the surface of the object 45. It is, however, possible to use other configurations of the detector. For example, a detection surface of a detector can be located close to the location 21 without surrounding the electron beam 13. Herein, the detector may have plural separate detection surfaces which are located close to the location 21 for detecting electrons and X-rays. Different membranes can be arranged in front of the plural detection surfaces in order to change the detection efficiency for electrons relative to a detection efficiency for X-rays of a respective detector. Moreover, the different detection surfaces may cover different amounts of solid angle relative to the location 21, such that an analysis of the detection signals of the different detectors allows to determine a three-dimensional structure of the sample.

Also, the four detectors 57 may all have same detection properties for electrons and X-rays. They will then differ by the fact that they cover different solid angles relative to the location 21 on the sample. The detectors will detect signals depending on an orientation of the surface of the sample at the location 21. Detection signals of the detectors may then be used to determine the three-dimensional structure of the sample. Background information relating to such determination of the three-dimensional structure can be obtained from the article "Three-Dimensional Characterization of Microstructures in a SEM", Wlodzimierz Drzazga et al., Meas. Sci. Technol. 17 (2006), pages 28-31.

In the illustrated example, the four membranes 61 arranged in front of the detection surfaces 59 of the four semiconductor detectors have different properties. Two different types of membranes are provided. Two membranes which are indicated by reference numeral 61 in FIG. 3 have a transmittance for secondary electrons which is greater than a transmittance for secondary electrons of the two other membranes which are indicated in FIG. 3 with reference numeral 61'.

The two different types of membranes having different transmittances for secondary electrons are provided to modify a detection efficiency for secondary electrons of the detector.

The membranes 61 can be made of a material including elements having a low atomic number such that a transmittance for X-rays is high. All membranes can be made from the same material and have different thicknesses for providing the different transmittances for secondary electrons. The membranes can be made of polyester, for example. Examples of suitable polyesters include terephtalat-polyester, such as polyethylenterephtalat-polyester. Suitable membranes can be obtained from the company DuPont, Wilmington, USA under the product name Mylar. Suitable thicknesses of the membranes can be, for example, within a range from 0.1 µm to 50 µm, and in particular from 1.0 µm to 10 µm. Other suitable membranes can be obtained from the company MoxTek, Orem, USA under the product name AP3.3. Still further membranes can be made of beryllium, for example.

In an exemplary embodiment illustrated with reference to FIGS. 4 and 5 below, a membrane having the greater transmittance for electrons is provided by a foil having a thickness of 1 µm made of the material AP3.3, and a membrane having a lower transmittance for electrons is made of a foil of a thickness of 6 µm of the material Mylar.

Figure 4:
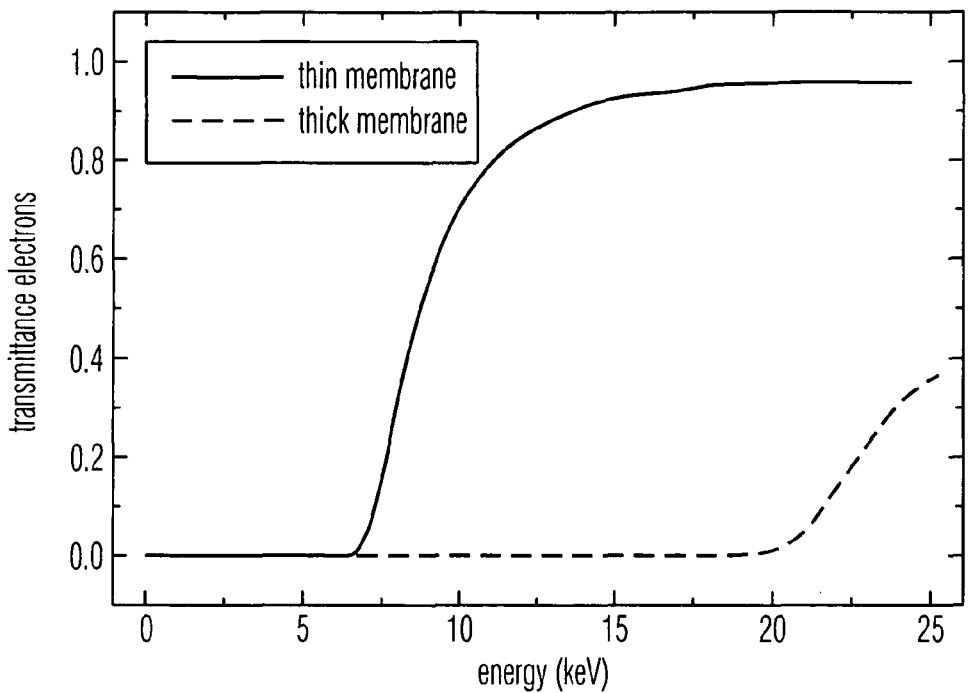
FIG. 4 is a graph representing a transmittance for electrons of membranes of the detector shown in FIGS. 2 and 3.

FIG. 4 shows a graph representing transmittances for electrons in dependence on the kinetic energy of the electrons for the two membranes obtained by numerical simulation.

Figure 5:
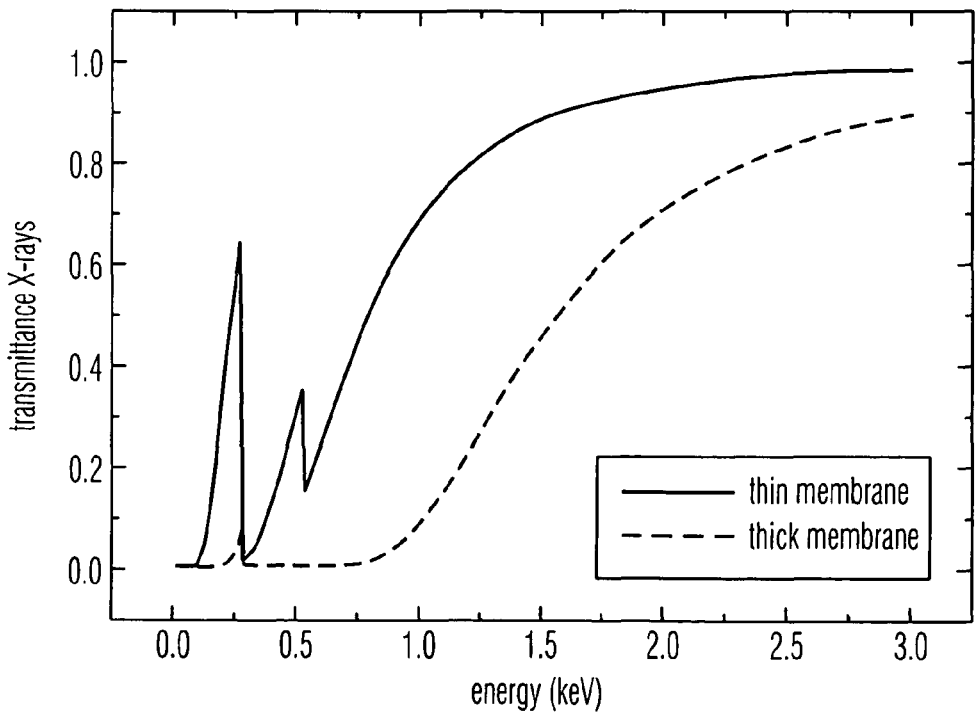
FIG. 5 is a graph representing a transmittance for X-rays of membranes of the detector shown in FIGS. 2 and 3.

FIG. 5 shows a graph representing transmittances for X-rays in dependence on kinetic energy of the electrons for the two membranes obtained by numerical simulation.

In the example illustrated with reference to FIG. 6 below, a membrane having the greater transmittance for electrons is provided by a foil of a thickness of 1 µm of Mylar material, and a membrane having the smaller transmittance for electrons is provided by a foil having a thickness of 6 µm of the same Mylar material.

Figure 6:
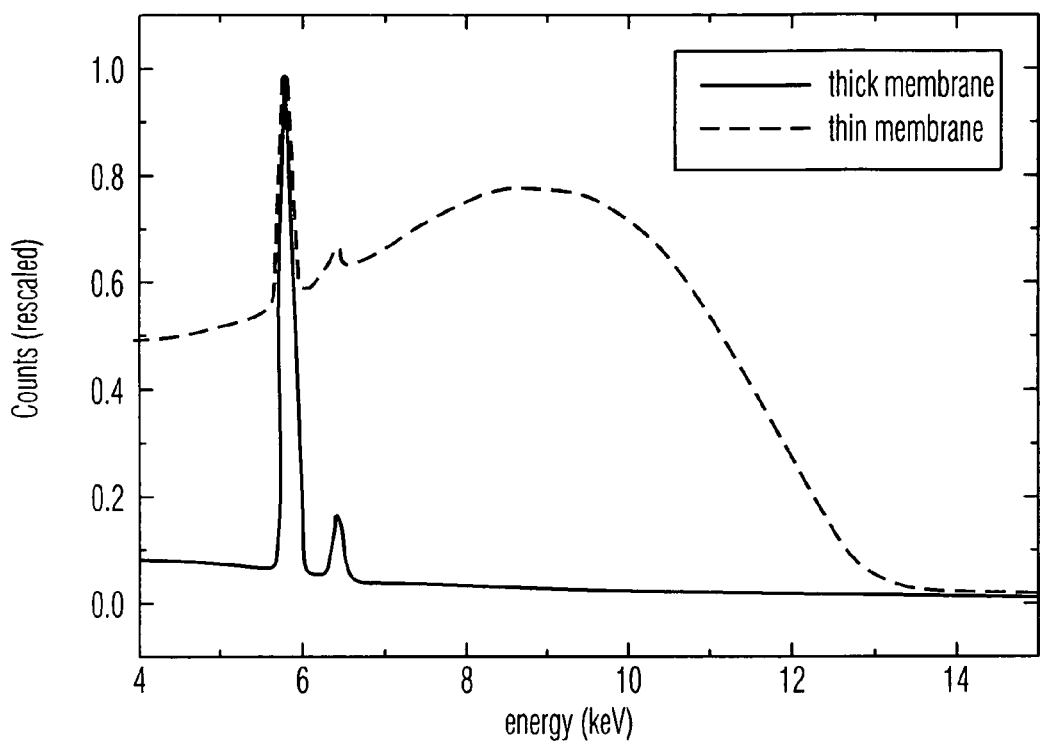
FIG. 6 is a graph representing count rates detected with the detector shown in FIGS. 2 and 3.

FIG. 6 shows graphs representing count rates measured in an experiment using the detectors 47 of the particle beam system 1 shown in FIG. 1. In this experiment, the primary particle beam is directed onto a sample made of manganese (Mn). The graphs shown in FIG. 6 illustrate a number of detection events recorded in a given time by the semiconductor detector having the thin foil located in front of it and a number of detection events recorded at the given time by the semiconductor detector having the thick foil located in front of it. Each graph is plotted in dependence on a kinetic energy of primary particles incident on the sample.

From FIG. 6 it is apparent that electrons do substantially not contribute to the energy spectrum of the thick membrane since this spectrum contains substantially only the narrow peaks characteristic of manganese, wherein a small amount of bremsstrahlung can be seen at low energies. For the thin membrane, the spectrum contains a higher number of components which include the components of the characteristic X-rays, the bremsstrahlung mentioned above and the additional component related to backscattered electrons detected by the detector. The backscattered electrons show a broad maximum at about 9 keV, wherein substantially no events are counted above 14 keV since the energy of the particles of the primary beam is 15 keV in the illustrated example.

Due to the different spectral properties of the electrons and the X-rays it is possible to separate electrons and X-rays from each other based on an analysis of the spectrum of detection events detected by the detector having the thin membrane arranged in front of its detection surface. It is possible to identify narrow peaks in the spectrum obtained with a thin membrane and to subtract the narrow peaks from the spectrum such that mainly the component related to backscattered electrons remains. This result can be further improved by considering the component related to bremsstrahlung. This component can be predicted with a relatively high accuracy from simulation and subtracted from the spectrum, such that the remaining spectrum will correspond to the signal component related to backscattered electrons with an even higher accuracy.

Figure 7:
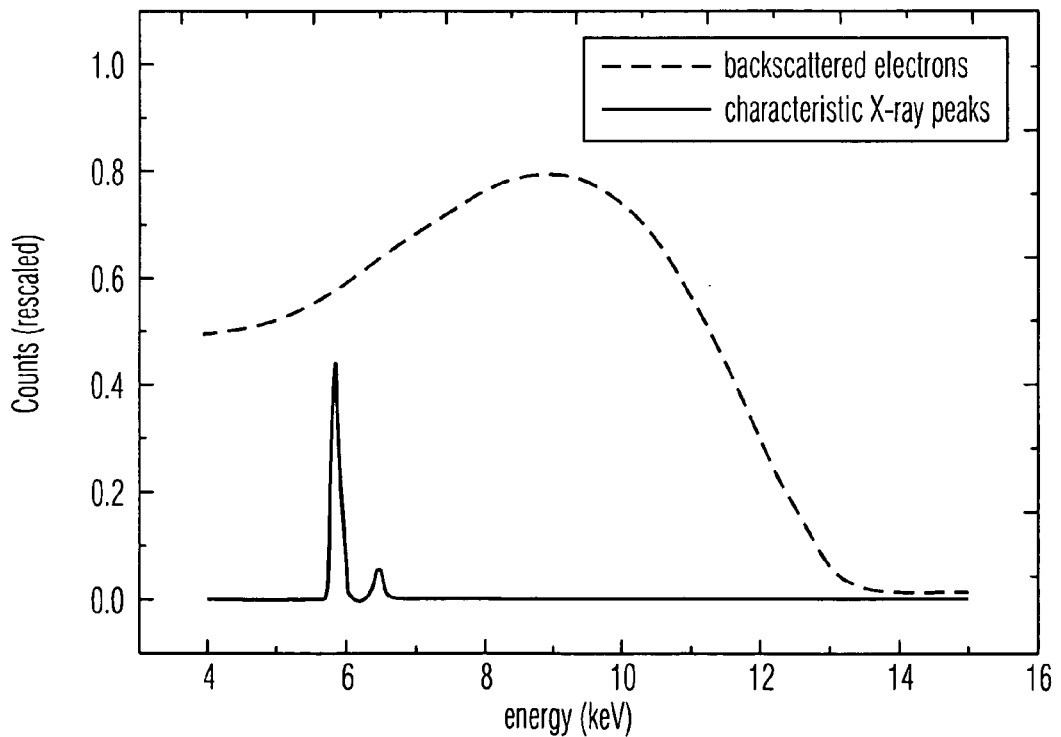
FIG. 7 is a graph representing for count rates generated by electrons and X-rays.

FIG. 7 shows a result of such analysis of the spectrum of the thin membrane shown in FIG. 6. The full line of FIG. 7 shows the X-ray spectrum, and the broken line in FIG. 7 shows the backscattered electron spectrum.

The X-ray spectrum can be further analyzed to determine chemical elements for which the spectrum is indicative. Background information relating to analyzing X-ray spectra with respect to elemental compositions of samples can be obtained from chapter 10.1 and 10.2 of L. Reimer, "Scanning Electron Microscopy", Second Edition, Springer 1998.

An integral or sum under the spectrum of the backscattered electrons shown in FIG. 7 corresponds to a backscattered electron (BSE) signal used in conventional electron microscopy.

By controlling the deflectors 41, it is possible to direct the particle beam 13 to plural different locations on the sample, and an energy spectrum can be recorded at each such location, wherein each energy spectrum will contain signal components related to electrons and signal components related to X-rays. The energy spectrum can be analyzed for each location to obtain the BSE signal and to generate and display an electron microscopic image of the sample based on the BSE signals of the plural locations. Similarly, the signal component related to X-rays can be obtained from the recorded energy spectra for each location. An elemental composition can be determined from the signal component related to X-rays. Information on the chemical composition at the plural locations can be used to produce a map of the chemical composition of the sample. Such map can be displayed on a display medium, such as a monitor, as a color representation, wherein different colors represent different chemical elements. It is also possible to display the map of the chemical composition in superposition with the electron microscopic image. If the detector has plural detection surfaces covering different solid angles about the location 21 of incidence of the primary beam, it is also possible to determine a three-dimensional surface structure of the sample from the different signal components of the plural detection surfaces. The three-dimensional structure can be also shown on the display medium, wherein it is possible to colorize the display of the three-dimensional structure according to the elemental composition.

Figure 8:
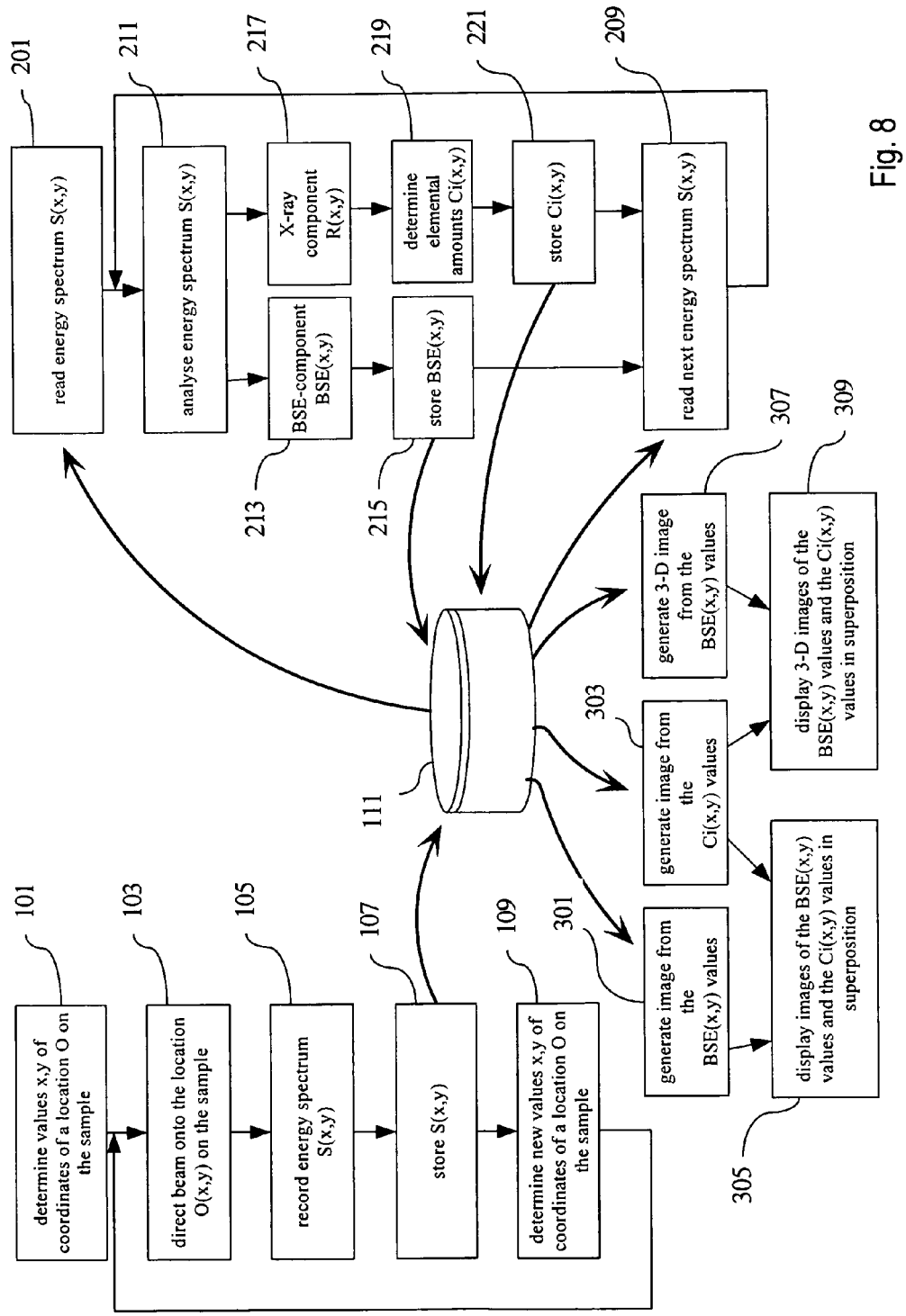
FIG. 8 is a flowchart of an inspection method according to an embodiment.

An embodiment of an inspection method will be summarized below with reference to the flowchart shown in FIG. 8. The method comprises determining a scan strategy according to which a surface of a sample is scanned with a focused particle beam. The focused beam can be scanned along a meander shaped path and it can be scanned line by line, for example. A starting value of a location on the sample at which the scanning starts is determine in an initial step 101. The location can be determined based on coordinates x, y on the sample or based on any other suitable coordinate system. Subsequent to the determination of the starting location, plural steps 103, 105 and 107 are repeatedly performed until a next location is determined in a step 109, wherein the steps 103, 105 and 107 will be again performed for the next location. The step 109 may also include termination of the repeated performance of steps 103, 105, 107 and 109, if the scanning of the sample is completed. In the step 103, the focused particle beam is directed to the location x, y on the sample. In the step 105, an energy spectrum $S(x,y)$ associated with this location is recorded by reading detection signals of the detector. The energy spectrum $S(x,y)$ will contain signal components related to electrons emanating from the locations $O(x,y)$ and signal components related to X-rays emanating from the location $O(x,y)$. In a step 107, the recorded spectrum $S(x,y)$ is stored on a storage medium 111, such as a computer disk drive.

The stored spectra are analyzed after completion of the scanning according to steps 101 to 109, or during such scanning. For this purpose, a computer reads a first spectrum in a step 201 and subsequent spectra in a step 209, in order to analyze the read spectra in steps 211 to 221 until all spectra recorded in the scanning are analyzed. The energy spectrum is analyzed in the step 211 in order to determine the signal components contained in the spectrum. Herein, the signal component related to backscattered electrons is extracted from the energy spectrum in a step 213, and a signal component related to X-rays is extracted from the energy spectrum in a step 217.

Step 213 further includes integrating the signal component related to backscattered electrons to determine a BSE-value associated with the location $O(x,y)$. This BSE-value $BSE(x,y)$ is stored on the storage medium 111 in a step 215. The signal component $R(x,y)$ related to X-ray is analyzed in step 219 in order to determine amounts $C_i$ of chemical elements at the location $O(x,y)$. The determined amounts $C_i(x,y)$ are stored on the storage medium 111 in step 221. The procedure of recording of the spectra in the steps 101 to 109 and the procedure of analyzing the spectra in the steps 201 to 221 are independently performed in the flow chart shown in FIG. 8. It is, however, also possible to transmit the spectra recorded in step 105 directly to the analyzing step 211 without storing in the storage medium 111.

Based on the BSE-values $BSE(x,y)$ associated with the different locations $O(x,y)$ it is possible to generate an electron-microscopic image of the scanned sample in a step 301. In a step 303, an image is generated from the values $C_i(x,y)$, wherein this image represents a distribution of chemical elements in the sample. The images generated in steps 301 and 303 can be displayed on the display 81 (FIG. 1) of the particle beam system. It is further possible to superimpose the images generated in steps 301 and 303 to form a common image in a step 305 and to display such image on display 81. This can be achieved by associating different colors with different chemical elements i and representing the amounts $C_i$ as intensities of the different colors. Such generated color image can be superimposed with the grey scale image obtained from the values BSE(x,y).

If the detector has plural detection surfaces covering different solid angles relative to the location of incidence of the particle beam, it is possible to determine the three-dimensional structure of the sample in a step 307. An image of the three-dimensional structure of the sample is superimposed with the chemical composition of the sample in a step 309. Again, this can be achieved by associating different colors with different chemical elements and colorizing the three-dimensional image according to these colors.

Embodiments of the inspection method and system allows for a simultaneous detection of backscattered electrons and X-rays generated by the incident focused particle beam. The signal components related to backscattered electrons and the signal components related to X-rays can be associated with a same location on the sample defined by the location of incidence of the primary particle beam. Herein, the backscattered electrons typically emanate from a volume around this location which is smaller than a volume from which the X-rays emanate. This is a reason why BSE images generally have a better spatial resolution than EDX images. According to the present embodiments it is, however, possible to improve a spatial resolution of detected EDX images based on structure information obtained from the BSE images. If, for example, a sample made of a first chemical element includes a narrow band formed of a second chemical element wherein a width of the narrow band is smaller than the spatial resolution of the EDX image but greater than the spatial resolution of the BSE image, it can be concluded from the BSE image that a detection signal related to the second chemical element can originate only from the narrow band having a width determined from the BSE image. This information can be used to improve the EDX image such that a width of the narrow band corresponding to the second chemical element as displayed in the image as reduced.

Since the X-rays emanate from a larger volume of the sample than the backscattered electrons, it is also possible to detect defects in the sample which are located below the surface of the sample and which would not be detected using only backscattered electrons. It is further possible to identify, by analyzing the BSE image, a region of the sample where a defect is potentially present, and to verify the presence of such defect by analyzing the corresponding X-ray spectra associated with that region.

Figure 9:
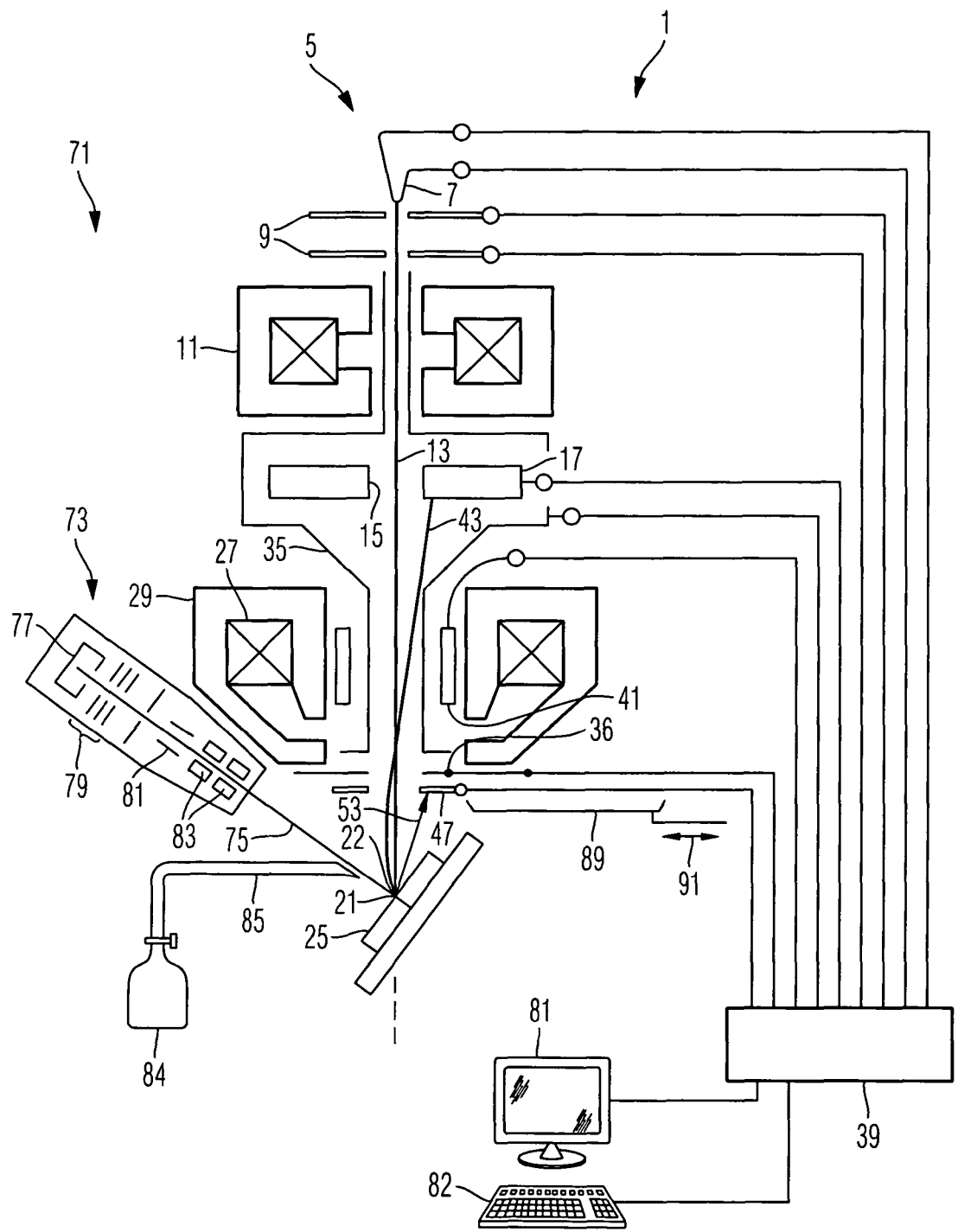
FIG. 9 shows a particle beam apparatus according to a further embodiment.

FIG. 9 is a schematic illustration of a particle beam apparatus 71 which can be used in a method of manufacture of an object. The particle beam apparatus 71 comprises a particle beam system 1 having a configuration similar to the particle beam system shown in FIG. 1. The particle beam system 1 comprises a particle beam source 5 generating a particle beam 13 which can be focused at a location 21 via lenses 11, 29. The particle beam apparatus 71 further comprises a second particle beam system 73 configured to focus a second particle beam 75 also at location 21. In the illustrated example, the particle beam system 73 is an ion beam system comprising an ion source 77 and electrodes 79 for shaping and accelerating the ion beam 75, and beam deflectors 81 and focusing coils or focusing electrodes 83 for focusing the ion beam 75 at the location 21 and to scan the beam across a region about location 21. The particle beams 75 and 13 will be incident under different angles of incidence on a common region of the sample 21 and can be scanned across this regions by controlling the deflectors 81 and 41, respectively. An angle between the directions of the particle beams 75, 13 can be 45°, for example. Examples of conventional systems providing two particle beams are disclosed in US 2005/0184251 A1 and U.S. Pat. No. 6,855,938, the full disclosure of which is incorporated herein by reference.

The particle beam apparatus illustrated with reference to FIG. 9 can be used in a method in which a thin plate or lamella 22 is manufactured from a sample 21 using the particle beam 75. The thin material plate or lamella 22 can be used as a sample in a subsequent inspection using a transmission electron microscope. For this purpose, the lamella should have a thickness of less than 1000 nm or less than 500 nm or even less than 200 nm. Conventional methods of manufacturing such thin material plates or lamellas are known from WO 2008/051937 A2 and WO 2008/051880 A2, the full disclosure of which is incorporated herein by reference.

In such methods, the thin lamella 22 is manufactured by etching from the bulk material of the sample 25. The etching comprises supplying a reactive gas from a reservoir 84 via a supply pipe 85 towards the lamella 22. The reactive gas is activated by the ion beam 75 close to the lamella, and reacts with the sample 22 in a region close to the location of incidence of the ion beam 75 on the sample 22. Due to such reaction, material of the sample is released from the sample and can be removed via a vacuum system of the particle beam apparatus. Accordingly, it is possible to remove material from selected regions of the sample by operating the ion beam system 73 and supplying reactive gas via the supply pipe 85. Such process can be observed using the particle beam system 1 by obtaining an electron microscopic image of the lamella 22 under preparation, wherein such electron microscopic image can be continuously recorded or can be recorded after a predefined number of etching steps. In such process, the particle beam system 1 is used as an imaging tool.

In such method, a thickness of the lamella under preparation can be determined based on detection signal components related to backscattered electrons and detection signal components related to X-rays. For this purpose, the particle beam 13 is directed to a location on the surface of the lamella. An intensity of the generated backscattered electrons is indicative of a thickness of the lamella since particles of the beam which are incident on and traverse a relatively thicker portion of the lamella will generate a greater amount of backscattered electrons than the particle beam incident on and traversing a relatively thinner portion of the lamella. However, the amount of backscattered electrons depends not only on the thickness of the lamella but also on the chemical composition of the lamella since different chemical elements produce different amounts of backscattered electrons upon irradiation with the particle beam 13. In the present embodiment, the chemical composition of the lamella at the location of incidence of the particle beam 13 can be determined by analyzing the detection signal components related to X-rays.

Therefore, it is possible to direct the particle beam onto a location on the surface of the lamella and to determine the chemical composition of the lamella at the location of incidence of the particle beam on the sample based on the analysis of the signal components related to X-rays. The information on the chemical composition can be used in an analysis of the intensity of the backscattered electrons to finally determine the thickness of the lamella at the location of incidence of the beam 13. Based on the determined thickness of the lamella it is then possible to decide whether the particle beam system 73 should be operated to further remove material from that location or not.

Since the chemical composition of the lamella may vary from location to location, it is possible to determine a thickness of the lamella at all locations with a relatively high accuracy since the chemical composition is taken into account.

In the illustrated method of manufacture, the removal of material is controlled based on detected electron intensities and detected X-ray intensities. A detector as illustrated with reference to FIGS. 1 to 7 above can be used to obtain the detected electron intensities and the detected X-ray intensities. Such detector is shown at 47 in FIG. 9, wherein the particle beam apparatus 71 further comprises a plate 89 which can be laterally displaced by an actuator as indicated by an arrow 91. Such that the plate 89 can be selectively positioned as shown in FIG. 9 and in a position in front of detector 47. In the position in front of the detector 47 the plate 89 covers the detector when seen from a location 22 of incidence of the particle beam 75. The plate 89 then prevents small particles released from the sample due to the operation of the particle beam system 73 from being incident on and damaging the detector 49. As an alternative to such protective plate 89 or in addition thereto, it is also possible to remove the detector 47 from its measuring position close to the sample when the particle beam system 73 is operated.

In the above illustrated example, the detector 47 is used to detect both electron intensities and X-ray intensities. It is, however, also possible to use separate detectors, i.e. an electron detector optimized for detecting electrons and substantially not detecting X-rays, and a separate X-ray detector optimized for detecting X-rays and substantially not detecting electrons.

The particle beam apparatus illustrated with reference to FIG. 9 above uses separate particle beam systems for removing material and for observing the material removal. It is, however, also possible to perform the material removal using other systems using other methods than the combination of a focused ion beam and the supply of a reactive gas, wherein the apparatus performing the material removal can be separate from the apparatus performing the imaging for monitoring the material removal wherein the sample can be transported back and forth between the apparatus for removal and the apparatus for imaging.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

What is claimed is:

1. An inspection method comprising:
   focusing a particle beam onto a sample;
   operating at least one detector located close to the sample;
   assigning detection signals generated by the at least one detector to different intensity intervals;
   determining, based on the detection signals assigned to the intensity intervals, at least one first signal component related to electrons incident on the detector; and
   determining, based on the detection signals assigned to the intensity intervals, at least one second signal component related to X-rays incident on the detector.

2. The inspection method according to claim 1, wherein, when the detection signals are represented as a spectrum in dependence of an intensity of the detection signals, the first signal component corresponds to a broad peak of the spectrum and the second signal component corresponds to a narrow peak of the spectrum.

3. The inspection method according to claim 1, further comprising determining at least one chemical element contained in the sample based on the at least one second signal component.

4. The inspection method according to claim 1, further comprising focusing the particle beam at plural different locations of the sample.

5. The inspection method according to claim 4, further comprising recording, for each of the plural locations of the sample, at least one first value which is determined based on the at least one first signal component and at least one second value which is determined based on the at least one second signal component.

6. The inspection method according to claim 4, further comprising generating a first map representing an electron microscopic image of the sample and generating a second map representing an image of an elemental composition of the sample.

7. The inspection method according to claim 6, further comprising displaying the first and second maps superimposed with each other on a display medium.

8. The inspection method according to claim 1, wherein the at least one detector is a semiconductor detector.

9. The inspection method according to claim 8, wherein the semiconductor detector is a silicon drift detector.

10. The inspection method according to claim 1, wherein at least one membrane is positioned between the sample and the at least one detector.

11. The inspection method according to claim 10, comprising operating first and second detectors, wherein a first membrane is positioned between the sample and the first detector, wherein a second membrane is positioned between the sample and the second detector and wherein the first and second membranes differ with respect to at least one of a thickness and an elemental composition.

12. The inspection method according to claim 11, wherein a thickness of the second membrane is at least 1.1 times greater than a thickness of the first membrane.

13. The inspection method according to claim 11, wherein a concentration of a chemical element present in the first membrane is at least 1.1 times greater than a concentration of the chemical element in the first membrane.

14. The inspection method according to claim 11, comprising:
   assigning detection signals generated by the first detector to different first intensity intervals;
   assigning detection signals generated by the second detector to different second intensity intervals;
   determining, based on the detection signals assigned to the first and second intensity intervals, the at least one first signal component related to electrons incident on the first and second detectors; and
   determining, based on the detection signals assigned to the first and second intensity intervals, at least one second signal component related to X-rays incident on the first and second detectors.

15. The inspection method according to claim 1, comprising operating plural detectors and determining a three-dimensional structure of the sample based on signal components determined from detection signals of the different detectors.

16. A particle beam system comprising:
   a particle beam source configured to generate a primary particle beam;

an objective lens configured to focus the primary particle beam in an object plane;

a detection system arranged between the objective lens and the object plane, the detection system comprising at least one detector; and a computer configured to analyze output signals of the at least one detector and to output a first value representing an electron intensity and a second value representing an elemental composition.

17. A method of manufacture of a miniaturized object, the method comprising:

focusing a particle beam onto a region of an object;

operating at least one detector located close to the object;

determining, based on detection signals received from the at least one detector, an amount of electrons emanating from the object due to the particle beam;

determining, based on detection signals received from the at least one detector, an amount of X-rays emanating from the object due to the particle beam;

determining, based on the determined amount of X-rays emanating from the object, a chemical composition of the object within the region of the object; and removing material from the object based on the determined amounts of electrons emanating from the object and the determined chemical composition of the object.

18. The method according to claim 17, wherein the removing of the material comprises focusing of an ion beam onto the region of the object.

19. The method according to claim 18, wherein the removing of the material comprises supplying a reactive gas to the region of the object.

20. The method according to claim 18, wherein the object has a thickness of less than 1 μm.

* * * * *